United States Patent [19]

Imperante et al.

[11] Patent Number: 5,286,830
[45] Date of Patent: Feb. 15, 1994

[54] SILICONE AMIDO TAURINE POLYMERS

[75] Inventors: John Imperante, Lebanon, N.J.; Anthony J. O'Lenick, Jr., Lilburn, Ga.

[73] Assignees: Siltech Inc., Norcross, Ga.; Phoenix Chemical, Somerville, N.J.

[21] Appl. No.: 51,097

[22] Filed: Apr. 22, 1993

[51] Int. Cl.$^5$ ............................................. C08G 77/04
[52] U.S. Cl. ...................................... 528/28; 556/419
[58] Field of Search ........................... 528/28; 556/419

[56] References Cited

U.S. PATENT DOCUMENTS 5,093,452  3/1992  O'Lenick, Jr. ...................... 556/419
5,115,049  5/1992  Imperante et al. .................. 556/419

Primary Examiner—Melvyn I. Marquis

[57] ABSTRACT

The present invention relates to a series of novel amido silicone functional taurine derivatives, useful in softening hair, and fiber and conditioning skin. The compounds of the present invention are prepared by the reaction of a carboxy silicone with a taurine derivative to produce novel surface active materials useful in personal care applications like soap bars.

18 Claims, No Drawings

SILICONE AMIDO TAURINE POLYMERS

BACKGROUND OF THE INVENTION

(1) Field of Invention

The present invention relates to a series of novel silicone derivatives of taurine having a fatty amido group present within the molecule. These materials are surface active silicone compounds which are useful in a personal care and related applications.

Since the compounds of the present invention are high molecular weight silicone polymers, they have a high degree of oxidative stability, even at elevated temperatures. In addition, these compounds are non volatile and non irritating to eyes and skin.

The compounds of the present invention are prepared by the reaction of a carboxy silicone with taurine.

(2) Object of the Invention

It is the object of the present invention to provide a series of novel silicone amido taurine polymers, which are substantive to skin and hair and useful in making soap bars.

This substantivity results in superior softening, conditioning and antistatic properties and results in a slick feeling soap bar.

It is another objective of the current invention to provide an amido silicone taurine derivatives which are nonirritating surface active agents. The compounds of the present invention have very low irritation values when applied to skin and eyes. Irritation is a major problem with traditional surfactants.

Application of the compounds of the invention can be from solvent, aqueous dispersion or solution, or applied neat in these process. It is anticipated that the effective conditioning concentration of the compound of this invention ranges from 0.1% to 25% by weight.

(3) Description of the Arts and Practices

Silicone oils (polydimethylsiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not bonded the effect is very transient. The product is removed with one washing. Taurine derivatives are known to those skilled in the art. Taurine conforms to the following structure:

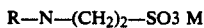

wherein R is alkyl, and M is a metal ion preferably an alkali metal such as sodium, potassium, ammonium or lithium.

None of the above incorporate silicone into compound. Consequently, the unique softening and substantivity properties achieved using the compounds of the present invention are not realized with the above technologies.

THE INVENTION

Summary of the Invention

The present invention relates to a series of novel amido silicone based taurine surfactants. These silicone polymers have a pendant taurine functional group present in am amido linkage to silicone. The polymers by virtue of the pendent group deposit on hair, skin and fiber surfaces forming effective nonvolatile nonirritating, surface modifying finishes. The compounds of the present invention are excellent conditioners, antistats and non-yellowing, softeners.

The products of the present invention are prepared by reaction of a carboxy containing silicone intermediate conforming to the following structure:

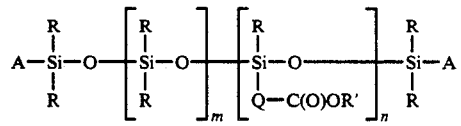

wherein;
R is methyl;
R' is hydrogen;
Q is $(CH_2)_c$;
c is an integer from 3 to 17:
A is methyl;
R' is hydrogen;
n is an integer from 1 to 10;
m is an integer from 1 to 200;
with a taurine derivative conforming to the following structure:

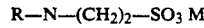

wherein
R is alkyl having 1 to 40 carbon atoms,
M is selected from the group consisting of Na, K, Li, and $NH_4$.

Or the products of the present invention are prepared by reaction of a carboxy containing silicone intermediate conforming to the following structure:

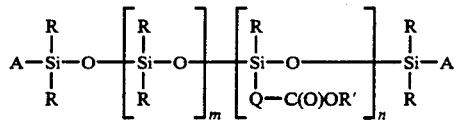

Wherein
R is methyl;
R' is hydrogen;
Q is $(CH_2)_c$;
c is an integer from 3 to 17;
n is 0;
A is —Q—C(O)OR'
m is an integer from 1 to 200;
with a taurine derivative conforming to the following structure:

wherein
R is alkyl having 1 to 40 carbon atoms,
M is selected from the group consisting of Na, K, Li, and NH4.

PREFERRED EMBODIMENTS

In a preferred embodiment n is 1.
In another preferred embodiment n is 2.
In another preferred embodiment n is 3.
In another preferred embodiment n is 4.
In the most preferred embodiment n is 10.
In a preferred embodiment R is alkyl having 12-18 carbon atoms.
In a preferred embodiment M is Na.
In another preferred embodiment M is K.

EXAMPLES

Carboxy Silicone Reactants

Many manufacturers offer a series of carboxy functional silicone compounds suitable for use as raw materials in the preparation of the esters of the present invention. These materials are marketed under the many trade names. Two companies making them are Siltech Inc, and Dow Corning.

The preferred method of placing this type of reactive carboxy group into the silicone polymer is by the reaction of silanic hydrogen containing polymer with a terminal unsaturated carboxylate. This technology is well known to those skilled in the art.

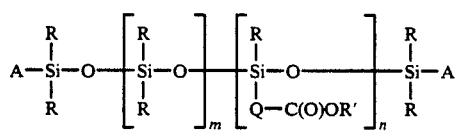

Wherein in
R is methyl;
R' is hydrogen;
Q is $(CH_2)_c$;
c is an integer from 3 to 17;
A is methyl;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1600 | 17 | 4 | 150 |
| 8 | Siltech C 1700 | 4 | 10 | 55 |

Terminal Substituted Carboxy Silicone

Terminal substituted carboxy silicone compounds are well known and are marketed in the trade under many names. The preferred method of placing this type of carboxyl group into the silicone polymer is by the reaction of terminal silanic hydrogen containing polymer with a terminal vinyl containing carboxy compound.

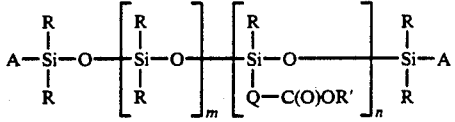

Wherein
R is methyl;
R' is hydrogen;
Q is $(CH_2)_c$;
c is an integer from 3 to 17;
n is 0;
A is —Q—C(O)OR'

| Example | Name | c | m |
|---|---|---|---|
| 9 | Siltech CT 701 | 10 | 1 |
| 10 | Siltech CT 706 | 3 | 200 |
| 11 | Siltech CT 710 | 17 | 50 |
| 12 | Siltech CT 750 | 10 | 100 |
| 13 | Siltech CT 790 | 3 | 150 |

Taurine Reactants

Alkyl taurine derivatives are commercially available from Nova Molecular Technologies, Janesville Wis.

These materials are prepared by the condensation of an amine with sodium isoethionate using an excess of the amine of about 6:1 to 2:1. The reaction is run at 230 C. for 6-24 hours removing water. The excess amine is distilled off under vacuum.

The reaction sequence is as follows:

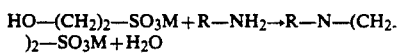

| Example | Designation | R Group | M Group |
|---|---|---|---|
| 14 | Sodium N-methyl Taurine | CH3 | Na |
| 15 | Sodium N-butyl Taurine | C4H9 | Na |
| 16 | Potassium N-hexyl Taurine | C6H13 | K |
| 17 | Potassium N-lauryl Taurine | C12H25 | K |
| 18 | Sodium N-palmityl Taurine | C16H37 | Na |
| 19 | Potassium N-stearyl Taurine | C18H37 | K |
| 20 | Sodium N-octyl-dodecyl Taurine | C20H41 | Na |
| 21 | Sodium N—C40H81 Taurine | C40H81 | Na |

COMPOUNDS OF THE PRESENT INVENTION

General Reaction Procedure

The products of the present invention are generally prepared as follows:

To a suitable flask, equipped with a thermometer and agitator is added the specified amount and the type of carboxy silicone. Next add the specified amount of the type of taurine reactant. Next add 54.0 grams of sodium hypophosphite, 98.0 grams of phosphoric acid and 24 grams of 50% sodium hydroxide. The reaction mass blanketed with nitrogen and heated to 220-240 C. and held from between 5 and 15 hours. water is distilled off which approaches 98% of theoretical before reaction is terminated.

The product can be used as prepared or washed with isopropanol and dried in vacuo.

EXAMPLE 22

To a suitable flask, equipped with a thermometer and agitator is added 609.0 grams type of carboxy silicone example 1. Next add 160.0 grams of taurine reactant example 14. Next add 54.0 grams of sodium hypophosphite, 98.0 grams of phosphoric acid and 24 grams of 50% sodium hydroxide. The reaction mass blanketed with nitrogen and heated to 220–240 C. and held from between 5 and 15 hours. Water is distilled off which approaches 98% of theoretical before reaction is terminated.

EXAMPLES 23–48

Example 22 is repeated only this time the specified amounts and types of silicone reactant and taurine derivative is added replacing the taurine and silicone reactant used in example 22.

|  | Taurine Reactants |  | Silicone Reactants |  |
|---|---|---|---|---|
| Example | Example | Grams | Example | Grams |
| 23 | 14 | 180.0 | 1 | 609.0 |
| 24 | 15 | 202.0 | 2 | 1827.0 |
| 25 | 16 | 246.0 | 3 | 1051.0 |
| 26 | 17 | 330.0 | 4 | 7570.0 |
| 27 | 18 | 337.0 | 5 | 2409.0 |
| 28 | 19 | 377.0 | 6 | 361.0 |
| 29 | 20 | 385.0 | 7 | 3100.0 |
| 30 | 21 | 625.0 | 8 | 524.2 |
| 31 | 14 | 160.0 | 9 | 290.0 |
| 32 | 15 | 202.0 | 10 | 7553.0 |
| 33 | 24 | 246.0 | 11 | 2200.0 |
| 34 | 16 | 330.0 | 12 | 4000.0 |
| 35 | 17 | 337.0 | 13 | 5700.0 |
| 36 | 18 | 377.0 | 1 | 609.0 |
| 37 | 19 | 385.0 | 2 | 1827.0 |
| 38 | 20 | 625.0 | 3 | 1051.0 |
| 39 | 21 | 160.0 | 4 | 7570.0 |
| 40 | 14 | 202.0 | 5 | 2409.0 |
| 41 | 15 | 246.0 | 6 | 361.0 |
| 42 | 16 | 330.0 | 7 | 3100.0 |
| 43 | 17 | 337.0 | 8 | 524.0 |
| 44 | 18 | 377.0 | 9 | 290.0 |
| 45 | 19 | 385.0 | 10 | 7553.0 |
| 46 | 20 | 625.0 | 11 | 2200.0 |
| 47 | 21 | 160.0 | 12 | 4000.0 |
| 48 | 14 | 202.0 | 13 | 5700.0 |

APPLICATIONS EXAMPLES

Several of the compounds of the present invention were milled into soap bars at 4%. The soap bar was found to have outstanding slip, lubrication and softening properties, without interfering with the bar's degree of solidness. The bars were rated on a scale of 1–5 for lubrications and softness. The results were as follows:

| 1 (worst) → 5 (best) | |
|---|---|
| Material | Rating |
| Soap Bar (no additive) | 1 |
| Example 23 | 4 |
| Example 40 | 4 |
| Example 48 | 5 |
| Example 26 | 3 |
| Example 35 | 3 |

As can be readily seen the addition of the compounds of the present invention to soap bars improves the soft hand and lubrication of the soap.

What is claimed;

1. A silicone taurine compound prepared by the reaction of a carboxy containing silicone compound conforming to the following structure:

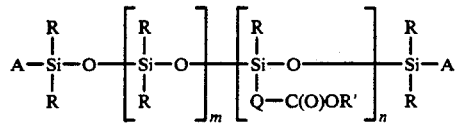

wherein;
R is methyl;
Q is $(CH_2)_c$;
c is an integer from 3 to 17;
A is methyl;
R' is hydrogen;
n is an integer from 1 to 10;
m is an integer from 1 to 200;
with a taurine derivative conforming to the following structure:

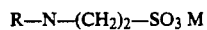

$$R-N-(CH_2)_2-SO_3 M$$

wherein
R is alkyl having 1 to 40 carbon atoms,
M is selected from the group consisting of Na, K, Li, and $NH_4$.

2. A silicone taurine compound of claim 1 wherein n is 1.

3. A silicone taurine compound of claim 1 wherein n is 2.

4. A silicone taurine compound of claim 1 wherein n is 3.

5. A silicone taurine compound of claim 1 wherein n is 4.

6. A silicone taurine compound of claim 1 wherein n is 10.

7. A silicone taurine compound of claim 1 wherein R is alkyl having 12–18 carbon atoms.

8. A silicone taurine compound of claim 1 wherein M is Na.

9. A silicone taurine compound of claim 1 wherein M is K.

10. A silicone taurine compound prepared by the reaction of a carboxy containing silicone compound conforming to the following structure:

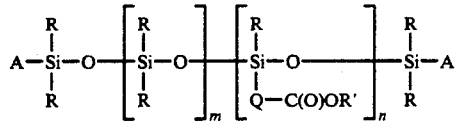

wherein
R is methyl;
R' is hydrogen;
Q is $(CH_2)_c$;
c is an integer from 3 to 17;
n is 0;
A is $-Q-C(O)OR'$
m is an integer from 1 to 200;
with a taurine derivative conforming to the following structure:

R—N—(CH$_2$)$_2$—SO$_3$ M wherein
R is alkyl having 1 to 40 carbon atoms,
M is selected from the group consisting of Na, K, Li, and NH$_4$.

11. A silicone taurine compound of claim 10 wherein n is 1.

12. A silicone taurine compound of claim 10 wherein n is 2.

13. A silicone taurine compound of claim 10 wherein n is 3.

14. A silicone taurine compound of claim 10 wherein n is 4.

15. A silicone taurine compound of claim 10 wherein n is 10.

16. A silicone taurine compound of claim 10 wherein R is alkyl having 12–18 carbon atoms.

17. A silicone taurine compound of claim 10 wherein M is Na.

18. A silicone taurine compound of claim 10 wherein M is K.

* * * * *